(12) United States Patent
Frigg

(10) Patent No.: US 6,607,531 B2
(45) Date of Patent: Aug. 19, 2003

(54) MEDULLARY NAIL FOR THE SURGICAL TREATMENT OF FOREARM FRACTURES

(75) Inventor: Robert Frigg, Bettlach (CH)

(73) Assignee: Synthes (USA), Paoli, PA (US)

( * ) Notice: Subject to any disclaimer, the term of this patent is extended or adjusted under 35 U.S.C. 154(b) by 64 days.

(21) Appl. No.: 09/858,585

(22) Filed: May 17, 2001

(65) Prior Publication Data

US 2001/0053912 A1 Dec. 20, 2001

Related U.S. Application Data

(63) Continuation of application No. PCT/CH98/00494, filed on Nov. 17, 1998.

(51) Int. Cl.[7] .................................................. A61B 17/72
(52) U.S. Cl. ......................................................... 606/62
(58) Field of Search .............................. 606/60, 62, 63, 606/64, 67, 68, 72

(56) References Cited

U.S. PATENT DOCUMENTS

| | | |
|---|---|---|
| 4,457,301 A | 7/1984 | Walker |
| 5,009,664 A | 4/1991 | Sievers ........................ 623/16 |
| 5,116,335 A | 5/1992 | Hannon et al. ................ 606/62 |
| 5,814,047 A | 9/1998 | Emilio et al. .................. 606/62 |
| 5,976,137 A * | 11/1999 | Mayer ......................... 606/62 |

FOREIGN PATENT DOCUMENTS

| | | |
|---|---|---|
| DE | 41 43 362 A1 | 1/1993 |
| EP | 0 551 846 A1 | 7/1993 |
| FR | 2 237 609 | 2/1975 |
| FR | 2 656 212 | 6/1991 |
| WO | WO 97/10767 | 3/1997 |
| WO | WO 98/24380 | 6/1998 |

* cited by examiner

Primary Examiner—David O. Reip
(74) Attorney, Agent, or Firm—Pennie & Edmonds LLP

(57) ABSTRACT

A medullary-space nail to surgically treat fracture of thin, tubular bones in the human body, comprising a nail shank having a longitudinal axis and an end part at its upper end fitted for engaging a tool, a longitudinal stem and a nail tip situated at the lower end to facilitate implantation. The stem includes channels running parallel to the longitudinal axis for receiving locking wires, in such manner that the locking wires can be displaced in the channels in the longitudinal direction and beyond the nail tip and can be screwed into the bone.

20 Claims, 2 Drawing Sheets

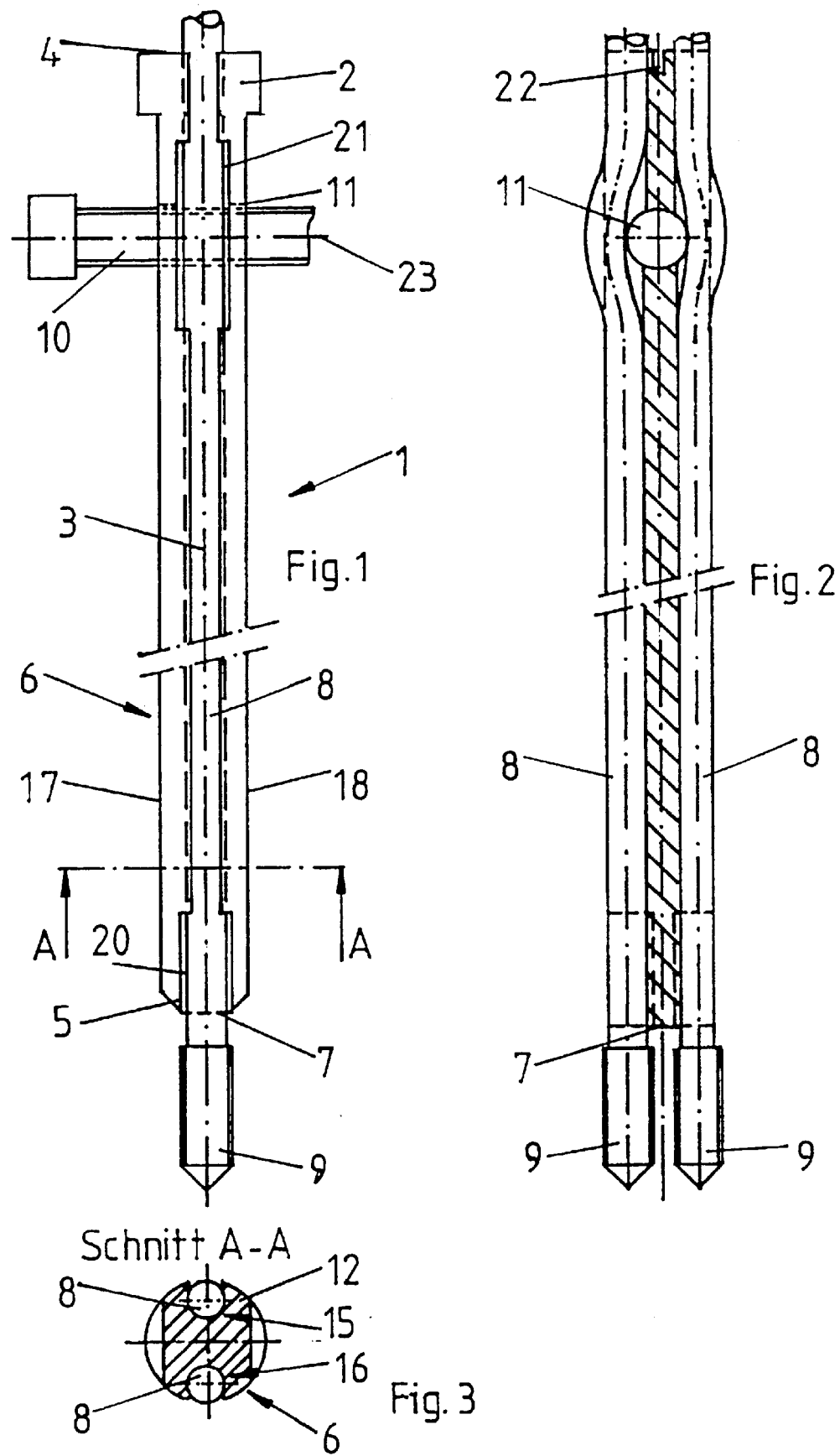

MEDULLARY NAIL FOR THE SURGICAL TREATMENT OF FOREARM FRACTURES

CROSS-REFERENCE TO RELATED APPLICATIONS

This application is a continuation of the U.S. National Stage designation of co-pending International Patent Application PCT/CH98/00494, filed Nov. 17, 1998, the entire content of which is expressly incorporated herein by reference thereto.

FIELD OF THE INVENTION

The invention relates to a medullary-space nail for the surgical treatment of fractures of thin tubular bones in the human body.

BACKGROUND OF THE INVENTION

Plates and screws are ordinarily used in the surgical treatment of forearm fractures. Contrary to the case of medullary nail treatment in other tubular bones (tibia, femur and humerus), treating the ulna or radius with medullary nails has not been widely accepted to date. In some cases pairs of thin medullary nails have been used and some bone splinting is made possible. However, rotation of the bone fragments cannot be prevented because the nails are not connected to each other. Moreover the medullary nails are affixed only by tensioning in the medullary space and outward migration of thin nails may raise problems. Experiments carried out with conventional locking nails have failed because a relatively small nail cross-section permits only minute cross-boreholes which are difficult to locate when the nail is inserted into the human body, even when using an image intensifier. Also, locking pins used with such nails are generally too small to absorb the generated forces.

One known medullary space nail is disclosed in U.S. Pat. No. 4,805,607 and has a non-circular, preferably triangular cross-section with concave sides. Using a reamer, this configuration of the medullary nail allows implantation in the medullary space of a bone without pre-drilling the medullary canal. The triangular nail allows cortical contact along three very thin metal edges. This localized configuration of the cortical contact reduces the danger that the medullary nail will rotate in the medullary space.

Another known medullary nail is disclosed in U.S. Pat. No. 5,116,335 and has a core and three flexible rods displaceable relative to the core. The core comprises three grooves situated on the circumference of the core spaced at 120° relative to each other and extending over the entire length of the core. Along the length of the core, the grooves have a cross-section that reduces toward the outer surface of the core and holds the rods. At the proximal and distal ends of the core, the cross-section of the grooves does not taper toward the outer surface, and the rods may be bent away transversely to the central axis for anchoring within the bone.

Yet, another medullary nail for the surgical treatment of forearm fractures, comprises a starshaped nail cross-section, and is marketed by Applied Osteo Systems Inc. of Walnut Creek, Calif. under the name of Trueflex Nail. Aside from splinting the bone, the star-shaped nail cross-section is intended to prevent the main fragments from rotating. However this result is only possible if the nail is struck as far as possible into the medullary space to anchor the nail tip in the spongy substance near the joint. However, the fracture zone can be stretched and fracture healing may be interfered with.

SUMMARY OF THE INVENTION

The medullary nail of the invention comprises a nail shank with channels running parallel and eccentrically to the longitudinal axis. The channels receive locking wires running parallel to the medullary nail and are rotatable inside the channels and can be translated in the longitudinal direction of the medullary nail. The channels define an opening along a longitudinal portion of the outside surface of the nail shank and the locking wires are prevented from moving out of the channels transversely to the longitudinal axis.

In one embodiment, the channels have an inside thread in the region of the lower end. In a preferred embodiment, the nail shank defines a throughbore in the vicinity of the upper end, and the throughbore has a central axis extending transversely to the longitudinal axis for receiving a locking screw therethrough to preclude displacement of the nail shank relative to the longitudinal axis as well as rotation of the nail shank about the longitudinal axis. The channels can have a recess in the region of the thoughbore, and the locking wires can be bendable around the locking screw.

In one preferred embodiment, the locking wires comprise threaded tips corresponding to the inside threads in the channels, and the tips are displaceable parallel to the longitudinal axis beyond the nail tip and screwable into the bone.

In another embodiment, the stem has an oblate cross-section with a perimeter including two parallel chord segments offset by a first distance and a pair of opposite semicircular surfaces having a first diameter. In one embodiment, the ratio of the first distance to the first diameter is in a range of about 0.50 to about 0.80. In another embodiment, the ratio of the first distance to the first diameter is in a range of about 0.60 to about 0.70.

In yet another embodiment, the channels are fitted into the peripheral arcs of circle of the cross-section. The end part can have a circular cross-section. The nail shank can be made of titanium, stainless steel, or plastic

BRIEF DESCRIPTION OF THE DRAWINGS

A preferred embodiment of the invention is elucidated below in relation to the drawings.

FIG. 1 is an elevation of the preferred embodiment of the medullary nail of the invention;

FIG. 2 is a longitudinal section of the medullary nail of the invention shown in FIG. 1;

FIG. 3 is a cross-section of the medullary nail of the invention shown in FIGS. 1 and 2.

DETAILED DESCRIPTION OF PREFERRED EMBODIMENTS

Figure 4:
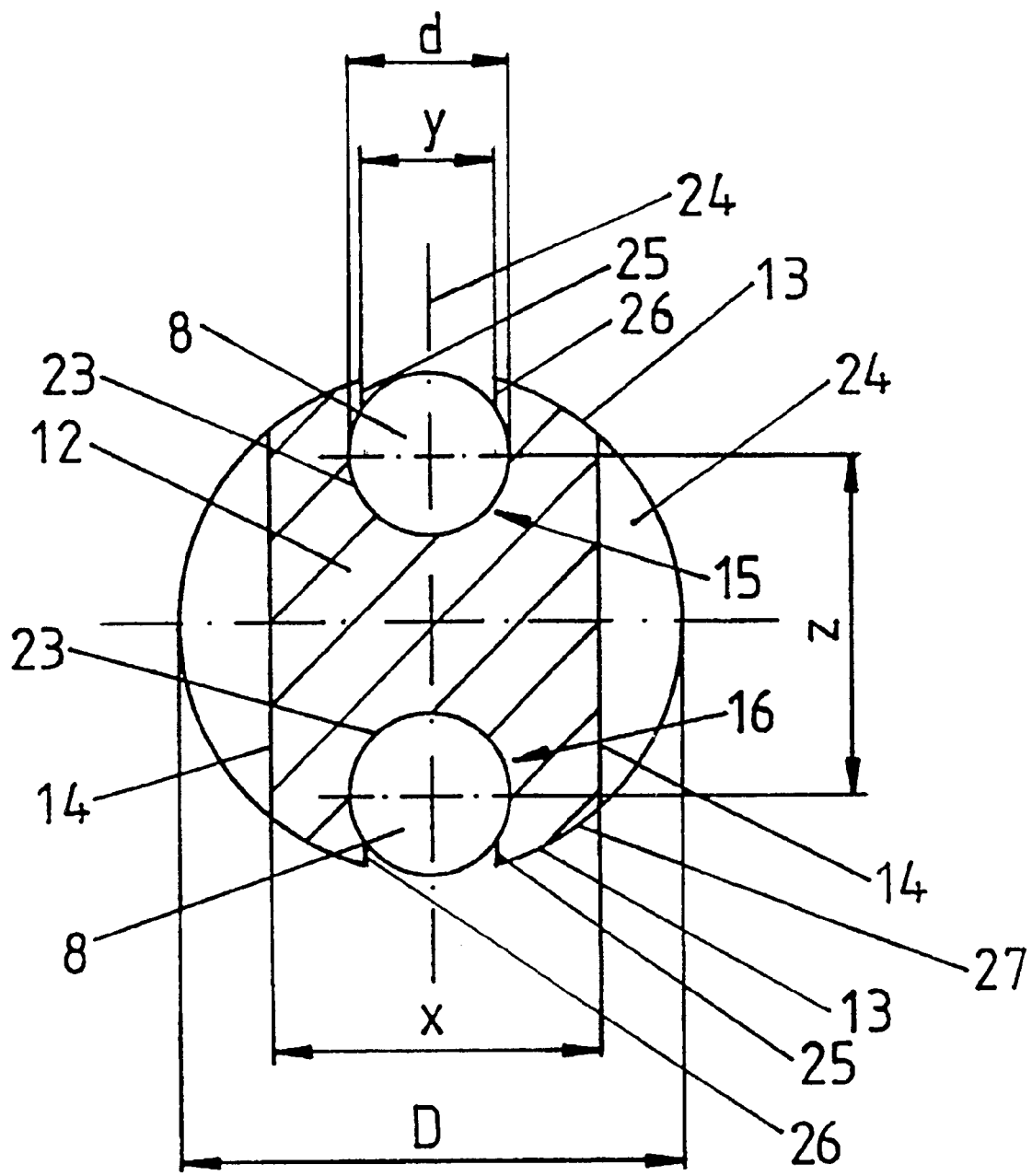
FIG. 4 is an enlargement of the cross-section of the medullary nail of the invention shown in FIG. 3.

The present invention is directed to a medullary nail for the treatment of bone fractures. The nail is preferably affixed to the bone and is prevented from rotating in the medullary space and preferably provides controlled and reliable intramedullar care of a bone fracture. The present invention is well suited for use in a thin tubular bone, for instance the radius, ulna or the tubular bones of children. In the preferred embodiment, the nail comprises a flexible implant and permits the selection of different entry sites (retrogradely, anterogradely). Excessive stretching of the fracture is correctable by retracting locking wires.

Aside from being used for the treatment of forearms (radius and ulna), the medullary nail of the present invention may also be used in fractures in the region of the thighs, lower legs and in the upper arm of children. Depending on the size and design of the thread at the tips of the locking wires, the fracture can be secured against rotation and axial butting while also permitting the tubular bone to grow because the nail is not locked with respect to traction and hence growth.

A preferred embodiment of the medullary nail of the invention is shown in FIGS. 1, 2, and 3 and comprises of a nail shank 1, a locking screw 10 and two locking wires 8. The nail shank 1 further comprises a longitudinal axis 3, an upper end 4, a lower end 5, a circular-cylindrical end part 2 at upper end 4 to connect to an assembly or disassembly tool, an adjoining stem 6, and a nail tip 7 at the lower end to facilitate implantation of the nail in bone. End part 2 preferably has a circular cross-section to allow connection to assembly or disassembly tools, however, a prismatic or cylindrical cross-section also may be applicable. The diameter D of circular-cylindrical end part 2 is preferably about 6 mm.

The stem 6 adjoining the end part 2 preferably has an oblate cross-section 12 relative to the end part 2. As shown cross-sectionally in FIG. 4, two segments with parallel chords 14 symmetrical to the longitudinal axis 3 are spaced preferably a distance 4 mm apart and are offset inward from the periphery 24 of end part 2. Two mutually diametrically opposite channels 15, 16 extend parallel to the longitudinal axis 3 and receive the locking wires 8. Referring to of the cross-section 12 in FIG. 4, channels 15, 16 are positioned in peripheral arcs of circle 13 of the shank between the chords 14 and are situated on a diametrical axis of symmetry 24. In this way, the locking wires are maximally spaced apart and the nail has a minimum nail cross-section, the channels are situated in the peripheral arcs of the circle 14 of the shank cross-section. The channels consist of boreholes 23 having a diameter d of about 2 mm and are spaced apart by a distance z of about 4 mm. In this manner the medullary nail may be made small and still permit controlled locking. In a preferred embodiment, the ratio of the distance x to the diameter D is in a range of about 0.50 to about 0.80, most preferably the ration is about 0.60 to about 0.70.

The channels 15, 16 are open in the direction of the peripheral arcs of circle 13 by means of parallel lateral surfaces 25, 26 respectively running in the direction of the longitudinal axis 3. The lateral surface 25, 26 are spaced apart by a distance y, preferably less than d, in the direction perpendicular to the longitudinal axis 3. Channels 15, 16 preferably narrow toward the outside surface 27 of the stem 6 and the locking wires 8 are displaceable in the direction of the longitudinal axis 3 inside the channels 15, 16 while being precluded from slipping out of them in a direction transverse to longitudinal axis 3.

The channels 15, 16 are fitted with inside threads 20 in the region of the lower end 5. Inside threads 20 cooperate with the outside threads at the threaded tips 9 of the locking wires 8. In this manner, the locking wires 8 together with the threaded tips 9 can be rotated back in the channels 15, 16 when the nail shank 1 is inserted into the medullary space. As a result the locking wires are retracted into the nail when the nail is inserted into the bone and will not snag during insertion into the medullary space.

Depending on the size of the medullary space, pre-drilling prior to the insertion of the medullary nail may not be required. For example, if the medullary space diameter is at least 6 mm, the medullary nail may be inserted into the medullary space without pre-drilling. Otherwise, the medullary space is preferably bored open.

Following implantation of nail shank 1, the locking wires 8 are rotated manually or by machine out of the nail shank 1 toward the nail tip 7 and can be screwed into the spongy substance and/or corticalis of the bone. The locking wires 8 are preferably substantially longer than the nail shank, and the depth of penetration in the metaphysis zone can be selected freely. Following the nailing process, the projecting ends of the locking wires can be severed. Once the locking wires have been anchored in the bone, the bone fracture gap can be closed by retracting the locking wires while simultaneously holding the nail shank in place.

After the nail is inserted and the fracture is reset, a proximal locking screw is set using an aiming device or x-ray monitoring. In this regard, the locking of the upper end 4 of nail shank 1 is implemented by a locking screw 10 inserted into the borehole 11 crossing the stem 6 transversely to the longitudinal axis 3. To prevent the locking wires 8 from covering the borehole 11, clearances 21 symmetrical to the borehole 11 are fitted in the channels 15, 16 to allow the locking wires 8 to move out of the channels 15, 16 and to permit the locking wires to be bent around the locking screw 10. Thus, when the locking screw is inserted into the upper end of the nail shank, the two locking wires are slightly bent outward, and are locked in place both rotationally and axially. Once this step has been carried out, the fracture is stabilized. The medullary nail is secured axially and rotationally by the two locking wires in one of the methaphyses and by the locking screw in the other metaphysis. Advantageously, the nail need not be forcefully struck into the bone in order to implement geometric locking. Also, small locking holes need not be searched for by x-rays or image intensification in the vicinity of the nail tip, and no screws are needed near the nail tip.

When the nail is used in porous bones, a bio-cement (for instance Norian or other degrading cements) may be additionally used. When injected in the diaphysis zone, this cement assures good anchoring of the locking wires 8 which nevertheless can be removed anytime by being rotated backward.

The material of the nail shank may be stainless steel, titanium, or, in the case of required high flexibility, also plastic. In one embodiment the shank can be made of a polyether ether ketone (PEEK) plastic. Moreover various materials may be combined with regard to the nail-shank material and that of the locking wires.

One of ordinary skill in the art can envision numerous variations and modifications to the invention disclosed herein. All of these modifications are contemplated by the true spirit and scope of the following claims.

What is claimed is:

1. A medullary-space nail for treatment of tubular bones in the human body, comprising:
    (a) a nail shank having a longitudinal axis, an upper end and a lower end, wherein,
    (b) the nail shank comprises an end part at the upper end to engage a tool, a longitudinal stem and a nail tip situated at the lower end for implantation into bone, and
    (c) the nail shank includes channels extending parallel and eccentric to the longitudinal axis for receiving locking wires, and to permit longitudinal movement of the locking wires in the channels and beyond the nail tip, wherein
        the channels define an opening along a longitudinal portion of an outside surface of the nail shank and the locking wires are retained within the channels in a direction transverse to the longitudinal axis.

2. The medullary nail of claim 1, wherein the channels have an inside thread in the region of the lower end.

3. The medullary nail of claim 1, wherein the nail shank defines a throughbore in the vicinity of the upper end, the throughbore having a central axis extending transversely to the longitudinal axis for receiving a locking screw therethrough to preclude displacement of the nail shank relative to the longitudinal axis as well as rotation of the nail shank about the longitudinal axis.

4. The medullary nail of claim 1, wherein said nail additionally comprises locking wires.

5. The medullary nail of claim 3, wherein the channels comprise a recess in the region of the throughbore, and the locking wires are bendable around the locking screw.

6. The medullary nail of claim 2, wherein said nail additionally comprises locking wires and the locking wires comprise threaded tips corresponding to the inside threads in the channels, said tips being displaceable parallel to the longitudinal axis beyond the nail tip and screwable into the bone.

7. The medullary nail of claim 1, wherein the stem has an oblate cross-section, and having a perimeter including two parallel chord segments offset by a first distance and a pair of opposite semi-circular surfaces having a first diameter.

8. The medullary nail of claim 7, wherein the ratio of the first distance to the first diameter is in a range of about 0.50 to about 0.80.

9. The medullary nail of claim 8, wherein the ratio of the first distance to the first diameter is in a range of about 0.60 to about 0.70.

10. The medullary nail of claim 7, wherein the channels arc adjacent the peripheral arcs of circle of the cross-section.

11. The medullary nail of claim 1, wherein the end part has a circular cross-section.

12. The medullary nail of claim 1, further comprising a locking screw.

13. The medullary nail of claim 1, wherein the nail shank is made of titanium.

14. The medullary nail of claim 1, wherein the nail shank is made of stainless steel.

15. The medullary nail of claim 1, wherein the nail shank is made of plastic.

16. The medullary nail of claim 15, wherein the medullary nail is made of a polyether ether ketone (PEEK) plastic.

17. The medullary nail of claim 1, wherein the end part has a prismatic cross-section.

18. A medullary-space nail for treatment of tubular bones in the human body, comprising:
   a nail shank having a longitudinal axis extending from an upper end to a lower end, wherein
      the nail shank comprises an end part at the upper end to engage a tool, a longitudinal stem and a nail tip situated at the lower end for implantation into bone, and
      the nail shank includes channels extending longitudinally through the shank and extending eccentric to the longitudinal axis; and
   locking wires insertable into the channels and configured and dimensioned to permit longitudinal movement therethrough, and each locking wire comprises a threaded tip, said threaded tip being displaceable beyond the nail tip and screwable into the bone to preclude rotation of the nail shank about the longitudinal axis.

19. The medullary nail of claim 18, wherein the nail shank defines a throughbore having a central axis extending transversely to the longitudinal axis for receiving a locking screw therethrough to preclude displacement of the nail shank relative to the longitudinal axis.

20. The medullary nail of claim 18, wherein the channels comprise a recess in the region of the thoughbore, and the locking wires are bendable around the locking screw.

* * * * *